Feb. 26, 1963 C. D. CORLISS Plant Pat. 2,231
EUONYMUS PLANT
Filed Oct. 23, 1961
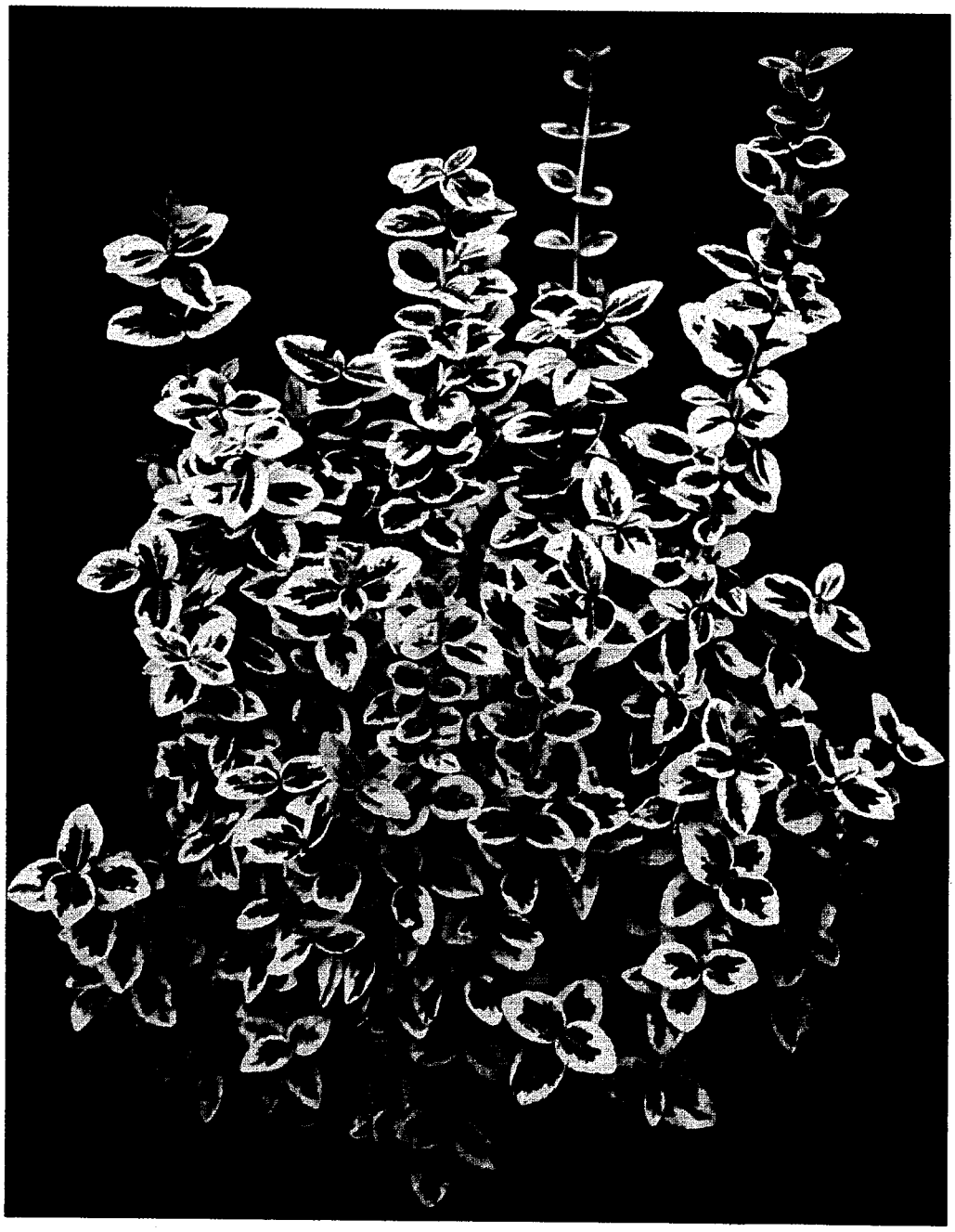
INVENTOR
Clifford D. Corliss
BY Robb & Robb
ATTORNEYS United States Patent Office Plant Pat. 2,231
Patented Feb. 26, 1963

2,231
EUONYMUS PLANT

Clifford D. Corliss, Gloucester, Mass., assignor to Corliss Bros., Inc., Gloucester, Mass., a corporation of Massachusetts Filed Oct. 23, 1961, Ser. No. 147,115
1 Claim. (Cl. 47—59)

The present invention relates to a new and distinct variety of Euonymus plant of the *Euonymus fortunei* species, which was discovered by me as a cultivated sport of the variety known as "Emerald Cushion" (Plant Patent No. 1,112).

At the time of my discovery aforesaid, a block of "Emerald Cushion" Euonymus plants were being grown under my direction and control in the branch nurseries of my assignee at Ipswich, Massachusetts. During one of my inspections of these plants, I discovered amongst the "Emerald Cushion" plants one particular plant which exhibited an unusual and abnormal habit of growth, as well as an unusual color of the foliage which was definitely different from the regular plants of the variety "Emerald Cushion." Upon closer examination of this particular plant, I found a plant of "Emerald Cushion" had sported, and I thereupon took steps to carefully preserve the sport, keep it under close observation, and later on asexually reproduced the same. Continued observations of the original sport, as well as the subsequent asexually reproduced plants thereof, convinced me that the sport is both new and distinct from the parent variety, as well as from all other varieties of Euonymus plants of which I am aware, as evidenced by the following unique combination of characteristics which are outstanding in the new variety and make it a very desirable plant for commercial purposes:

(1) A distinctly upright habit of growth, in contrast to the low and wide type of growth that is characteristic of the parent variety;

(2) Attractive compact shape which has great ornamental value throughout the year;

(3) Good winter hardiness, as evidenced by the fact that unprotected plants grown outdoors have withstood winter temperatures as low as 10° below zero without injury; and (4) A distinctive and unusual green and yellow variegation of the foliage which gives the entire plant a distinct and attractive golden appearance.

Asexual reproduction of my new variety by cuttings, as performed at Ipswich and Gloucester, Massachusetts, shows that the foregoing characteristics and distinctions come true to form and are established and transmitted through succeeding propagations.

The accompanying drawing shows a typical two-year old specimen plant of my new variety as depicted in color as nearly true as it is reasonably possible to make the same in a color illustration of this character.

The following is a detailed description of my new variety, with color terminology in accordance with Nickerson's Color Fan, as published by Munsell Color Company, Inc., of Baltimore, Maryland, except where general color terms of ordinary dictionary significance are obvious:

Form: Erect; dense; compact; slow growing; not as low or as broad as the parent variety "Emerald Cushion."

Growth:

*Two-year old plants.*—Height—from about 15 to 18 inches. Breadth—from about 12 to 15 inches.

*Mature plants.*—Height—from about 3 to 4 feet. Breadth—from about 2½ to 3 feet.

Hardiness: Good tolerance to extremely low temperatures, as evidenced by the fact that plants without winter protection have withstood below zero weather in northeastern Massachusetts with no sign of winter burn or defoliation.

Stems (branchlets): Minutely warty. Color: Lower branches—light green, shaded to Moderate Yellow Green, Plate 5GY 5/6. Newer growth—pronounced variegated Strong Yellow Green, Plate 2.5GY 6/8.

Axillary buds: Elongate; conical.

Foliage:

*Type.*—Broadleaf evergreen; petioled; opposite.

*Shape.*—From ovate to broad ovate, with apex obtuse and less frequently emarginate than parent variety "Emerald Cushion."

*Petioles.*—Length—from 3 to 5 mm. Color—same as stems.

*Size of leaf.*—Length—from 2 to 3½ cm. Breadth—from 1½ to 2½ cm.

*Leaf texture.*—Thin; leathery; smooth.—Upper surface—glossy. Under surface—dull.

*Veining.*—Midrib on underside frequently visible, but lateral veins difficult to see; on upper surface, midrib and sometimes the lateral veins are clearly visible and pronounced, and are of a lighter color than the surrounding areas of the leaf.

*Serrations.*—Crenate-serrate margins, rather than crenate-dentate margins of leaves of parent variety "Emerald Cushion."

*Color.*—Mature leaves: upper surface—from Moderate Olive-Green, Plate 5GY 4/3 to Strong Yellow Green, Plate 5GY 6/8, with variegated margins of cream and ivory colors which frequently extend over most of the leaf; under surface—similar but lighter colors. New leaves: upper surface—Strong Yellow Green, Plate 5GY 6/8 with marginal variegations Brilliant Yellow, Plate 2.5Y 9/9, which gives the entire plant a distinct golden appearance; under surface—similar but lighter colors. Inner leaves: variegations on leaves inside the plant are frequently Strong Yellow Green, Plate 5GY 6/8.

I claim:

A new and distinct variety of Euonymus plant of the *Euonymus fortunei* species, substantially as herein shown and described, characterized particularly as to novelty by the unique combination of an upright habit of growth which is shapely, compact and attractive in form, good winter hardiness, and attractive thick broadleaf evergreen foliage of rich Deep Green general color tonality having pronounced variegated margins of irregular depth ranging from Brilliant Yellow to cream and ivory, with the leaves inside the plant frequently colored Strong Yellow Green, and with the aforementioned colors giving to the plant as a whole a distinctive and striking golden appearance.

No references cited.